United States Patent

Andou et al.

[11] Patent Number: 5,961,881
[45] Date of Patent: Oct. 5, 1999

[54] LIQUID CRYSTAL COMPOSITION AND LIQUID CRYSTAL DISPLAY ELEMENT

[75] Inventors: Tugumiti Andou, Kumamotoken; Koichi Shibata, Chibaken; Shuichi Matsui, Chibaken; Kazutoshi Miyazawa, Chibaken; Hiroyuki Takeuchi, Chibaken; Yasusuke Hisatsune, Chibaken; Fusayuki Takeshita, Chibaken; Etsuo Nakagawa, Chibaken; Katsuhiko Kobayashi, Chibaken; Yoshitaka Tomi, Chibaken, all of Japan

[73] Assignee: Chisso Corporation, Osaka, Japan

[21] Appl. No.: 08/966,417

[22] Filed: Nov. 7, 1997

[30] Foreign Application Priority Data

Nov. 22, 1996 [JP] Japan ................................. 8-327854
Oct. 15, 1997 [JP] Japan ................................. 9-297680

[51] Int. Cl.⁶ ..................... C09K 19/30; C09K 19/12; C09K 19/20; C09K 19/06
[52] U.S. Cl. ..................... 252/299.63; 252/299.66; 252/299.67; 252/299.6
[58] Field of Search ................ 252/299.63, 299.66, 252/299.67, 299.6

[56] References Cited

U.S. PATENT DOCUMENTS

| | | | |
|---|---|---|---|
| 5,045,229 | 9/1991 | Bartmann et al. | 252/299.01 |
| 5,589,102 | 12/1996 | Bartmann et al. | 252/299.01 |
| 5,728,319 | 3/1998 | Matsui et al. | 252/299.63 |
| 5,792,386 | 8/1998 | Matsui et al. | 252/299.01 |

FOREIGN PATENT DOCUMENTS

| | | |
|---|---|---|
| 0387032 | 9/1990 | European Pat. Off. . |
| 19531165 | 3/1996 | Germany . |
| 2-233626 | 9/1990 | Japan . |
| 2229438 | 9/1990 | United Kingdom . |
| WO94/03558 | 2/1994 | WIPO . |
| WO 96/11897 | 4/1996 | WIPO . |
| WO 96/11994 | 4/1996 | WIPO . |

*Primary Examiner*—C. H. Kelly
*Attorney, Agent, or Firm*—Wenderoth, Lind & Ponack, L.L.P.

[57] ABSTRACT

There is provided a liquid crystal composition in particular with a low threshold voltage and a wide range of nematic phase temperature (with high TNI point and low TC), while satisfying various properties required for liquid crystal compositions for active matrix type liquid crystal display elements. The composition contains, for example, compounds represented by general formulas (1-1) and (2-1):

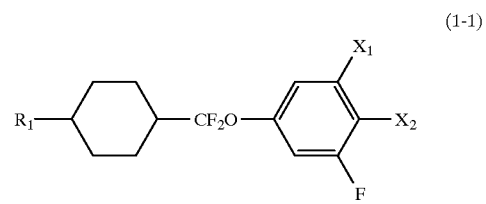

(1-1)

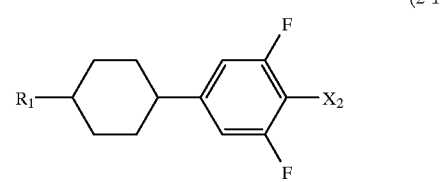

(2-1)

where each $R_1$ independently represents an alkyl group having 1 to 10 carbon atoms; $X_1$ represents H or F; and each $X_2$ independently represents F, $OCF_3$, $CF_3$, or $OCF_2H$.

6 Claims, No Drawings

LIQUID CRYSTAL COMPOSITION AND LIQUID CRYSTAL DISPLAY ELEMENT

TECHNICAL FIELD

The present invention relates to a liquid crystal composition for liquid crystal display using the active matrix system, and to a liquid crystal display element produced from such a liquid crystal composition.

BACKGROUND ART

In comparison to a display using a cathode ray tube, a liquid crystal display element (LCD) consumes less electric power and is smaller and lighter. Systems in practical use that utilize such advantages include the twist nematic system, in which the twist angle between alignment layers of upper and lower substrates is 90 degrees; the super twist nematic system, in which the twist angle between alignment layers of upper and lower substrates is 180–260 degrees; and the in-plane switching system, in which the twist angle between alignment layers of upper and lower substrates is 0 degrees. In the twist nematic system and the in-plane switching system, liquid crystals are driven by the MIM system using a two-terminal thin layer transistor, and the TFT system using a three-terminal thin film transistor. (The MIM and TFT systems are collectively called the active matrix system.)

Properties required by liquid crystal compositions used in active matrix type display elements include:

(1) high specific resistance of the liquid crystal composition itself, and high voltage retention in the cell of the liquid crystal display element;
(2) wide nematic-phase range of the liquid crystal composition itself;
(3) the anisotropy in the refractive index of the liquid crystal composition can be changed adequately according to the cell thickness of the liquid crystal display element; and
(4) the threshold voltage of the liquid crystal composition itself can be changed adequately according to the drive circuit of the liquid crystal display element.

In recent years, notebook-type portable personal computers which can be used outdoors have been developed, and the use of LCDs has been widespread. As compared with LCDs for indoor machines, LCDs for portable machines are restricted in driving power sources. In order that an LCD can be driven outdoors for a long time, the power consumption of the LCD must be decreased. In order that the power consumption of the LCD can be decreased, the threshold voltage of the liquid crystal composition itself must be decreased.

In view of such a background, Japanese Patent Application Laid-open No. 2-233626 discloses a trifluoro compound whose relatively large anisotropy of inductivity is suitable for a liquid crystal compound for active matrix type display elements. Application Example 2 of the above Patent Application discloses a composition comprising 15 percent by weight of a trifluoro compound and 85 percent by weight of a difluoro compound. However, the threshold voltage of the liquid crystal composition of this Example is high, making this composition unsuitable for fabricating portable LCDs.

WO94/03558 discloses a composition comprising trifluoro and difluoro compounds. In liquid crystal compositions disclosed in Examples 1 and 2 of the above patent, the upper temperature limit of the nematic liquid crystal phase is as low as 50° C., and in Example 4 of the above patent, the threshold voltage is high. Therefore, this liquid crystal composition is not suitable for fabricating portable LCDs.

Although liquid crystal compositions have been intensively studied to meet various purposes, new improvement is always required.

An object of the present invention is to provide a liquid crystal composition which has in particular a low threshold voltage and a wide temperature range of the nematic phase, while maintaining various properties required for liquid crystal compositions for active matrix type display elements.

DISCLOSURE OF INVENTION

To solve the above problems the inventors of the present invention conducted repeated examinations of liquid crystal compositions comprising various liquid crystal compounds, and found that the above object was achieved when a liquid crystal composition according to the present invention is used for fabricating an active matrix type display element.

The above problems have been solved by the present invention by adopting the following constitution.

According to a first aspect of the present invention, there is provided a liquid crystal composition containing at least one of compounds represented by general formulas (1-1) and (1-2) as a first component, and at least one of compounds represented by general formulas (2-1) through (2-8) as a second component.

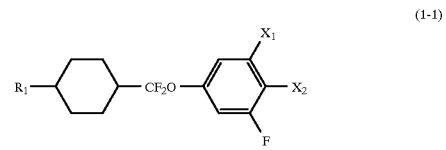

(1-1)

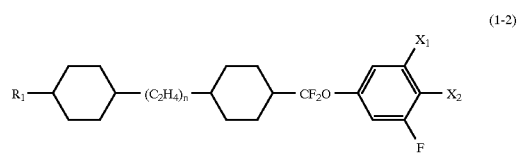

(1-2)

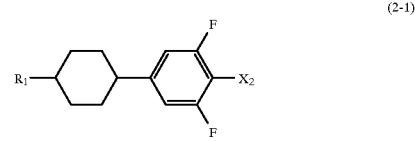

(2-1)

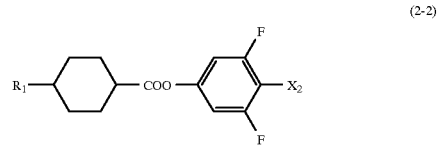

(2-2)

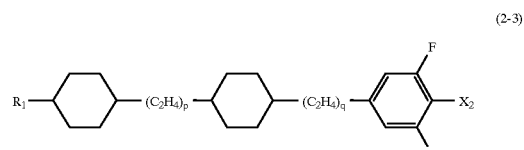

(2-3)

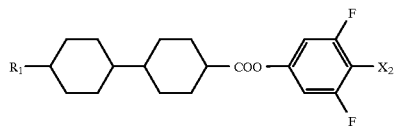

(2-4)

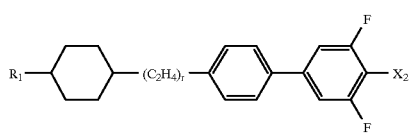

(2-5)

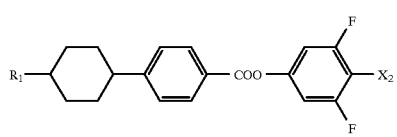

(2-6)

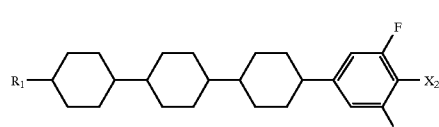

(2-7)

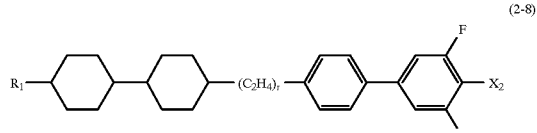

(2-8)

where each $R_1$ independently represents an alkyl group having 1 to 10 carbon atoms; each $X_1$ independently represents H or F; each $X_2$ independently represents F, $OCF_3$, $CF_3$, or $OCF_2H$; n represents 0 or 1; p and q independently represent 0 or 1; the sum of p and q is 1 or less; and each r independently represents 0 or 1.

According to a second aspect of the present invention, there is provided a liquid crystal composition according to the first aspect, wherein the total amount of compounds represented by general formulas (1-1) and (1-2) is 3 to 70 percent by weight relative to the total weight of the liquid crystal composition, and the total amount of compounds represented by general formulas (2-1) through (2-8) is 30 to 97 percent by weight relative to the total weight of the liquid crystal composition.

According to a third aspect of the present invention, there is provided a liquid crystal composition containing at least one of compounds represented by general formulas (1-1) and (1-2) in an amount of 3 to 70 percent by weight relative to the total weight of the liquid crystal composition as a first component, at least one of compounds represented by general formulas (2-1) through (2-8) in an amount of 27 to 94 percent by weight relative to the total weight of the liquid crystal composition as a second component, and at least one of compounds represented by general formulas (3-1) and (3-2) in an amount of 3 to 50 percent by weight relative to the total weight of the liquid crystal composition as a third component.

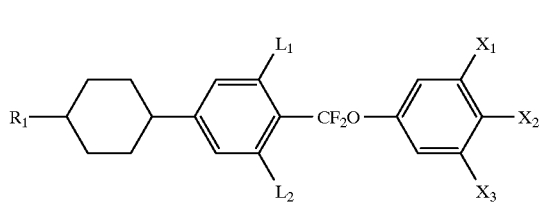

(3-1)

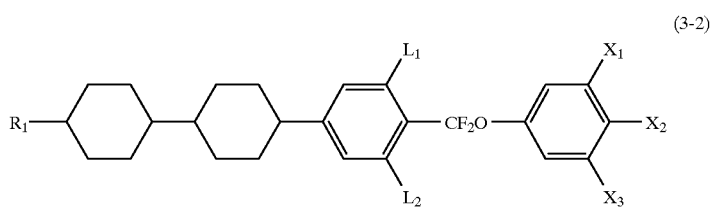

(3-2)

where each $R_1$ independently represents an alkyl group having 1 to 10 carbon atoms; $L_1$ and $L_2$ independently represent H or F; $X_1$, and $X_3$ independently represent H or F; and each $X_2$ independently represents F, $OCF_3$, $CF_3$, or $OCF_2H$.

According to a fourth aspect of the present invention, there is provided a liquid crystal display element produced from a liquid crystal composition according to any of the first through third aspects.

As the compounds represented by the general formula (1-1) of the present invention, compounds represented by the following general formulas (1-1-1) through (1-1-8) are preferably used.

As the compounds represented by the general formula (1-2) of the present invention, compounds represented by the following general formulas (1-2-1) through (1-2-16) are preferably used.

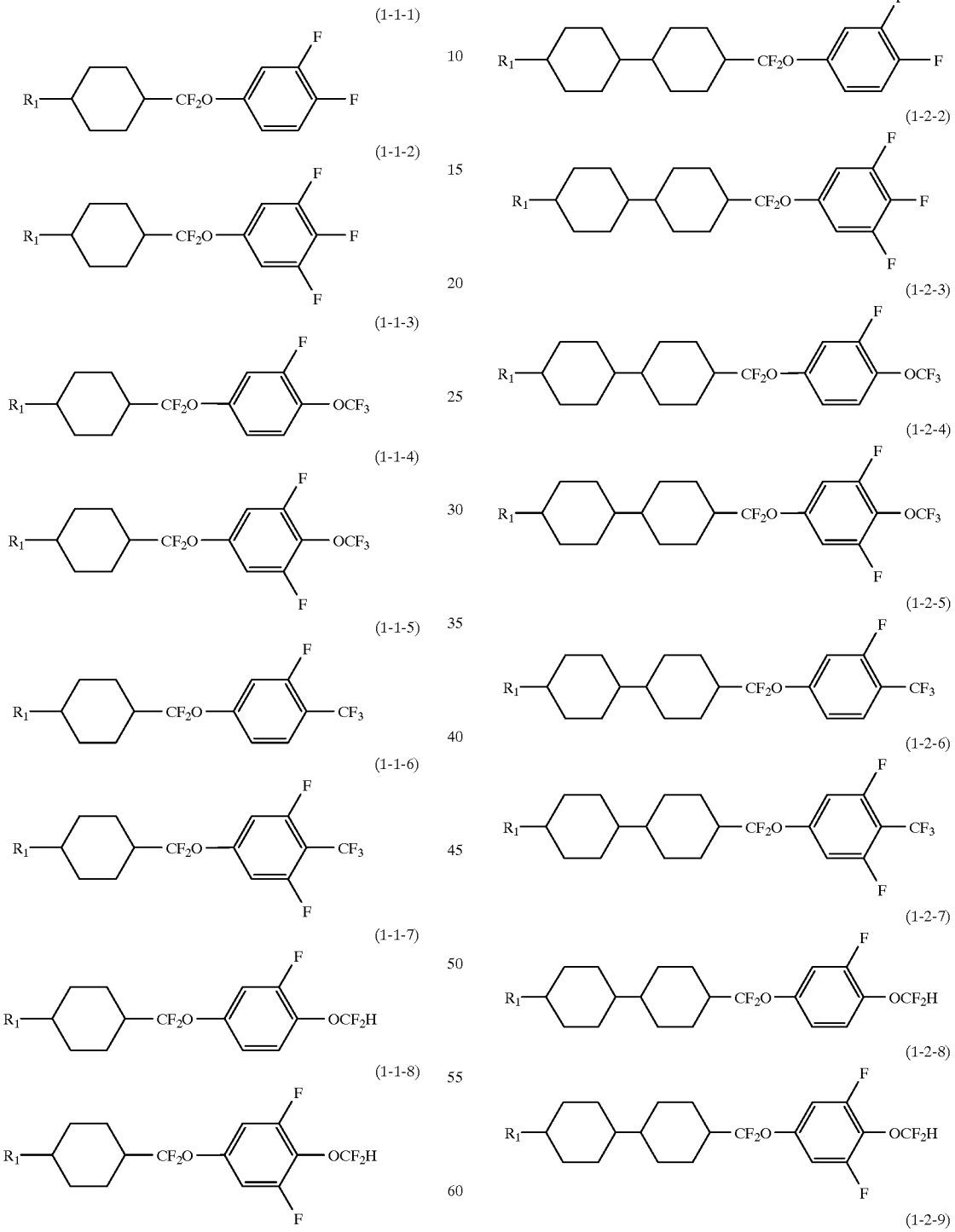

where $R_1$ is as described above.

Among these compounds, compounds represented by the general formulas (1-1-1), (1-1-2), and (1-1-3) are particularly preferable.

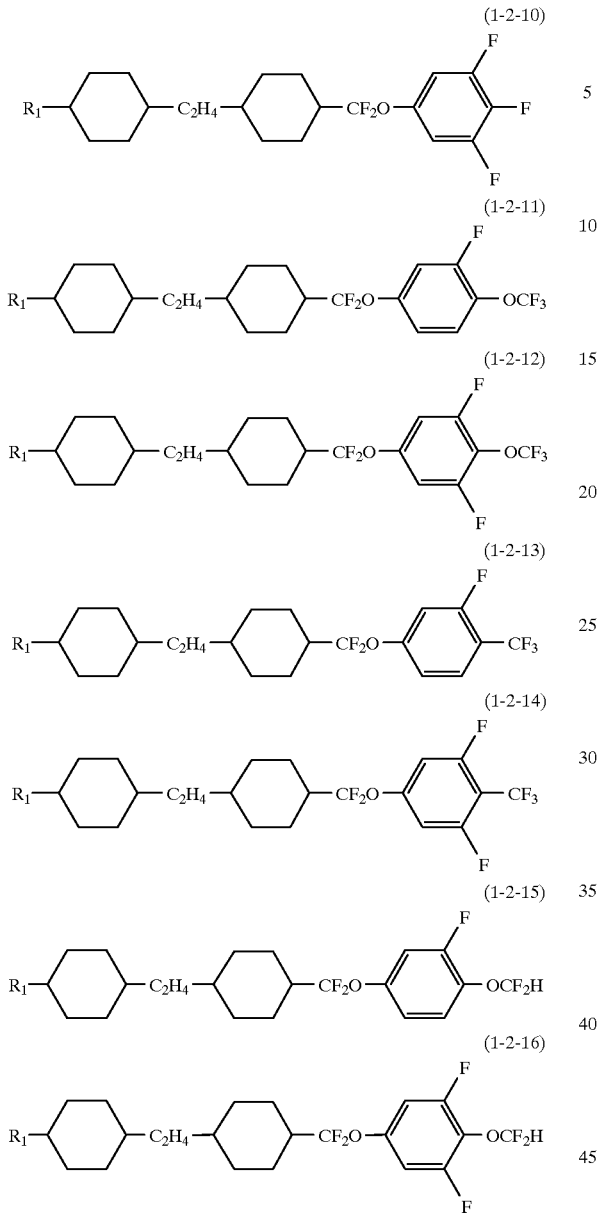

where $R_1$ is as described above.

Among these compounds, compounds represented by the general formulas (1-2-1), (1-2-2), (1-2-3), (1-2-9), (1-2-10), and (1-2-11) are particularly preferable.

As the compounds represented by the general formula (2-1) of the present invention, compounds represented by the following general formulas (2-1-1) through (2-1-4) are preferably used.

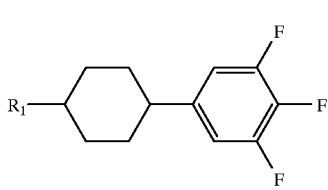

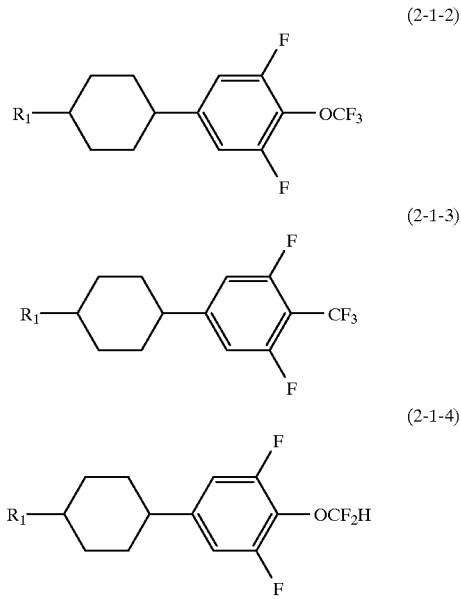

where $R_1$ is as described above.

Among these compounds, compounds represented by the general formula (2-1-1) are particularly preferable.

As the compounds represented by the general formula (2-2) of the present invention, compounds represented by the following general formulas (2-2-1) through (2-2-4) are preferably used.

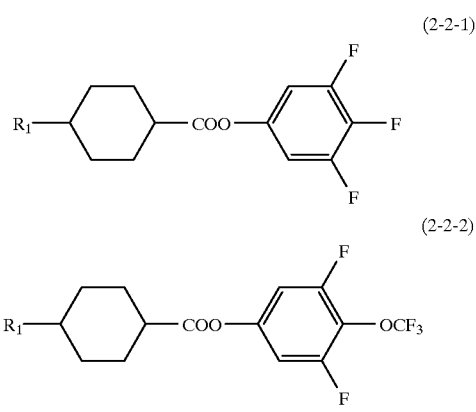

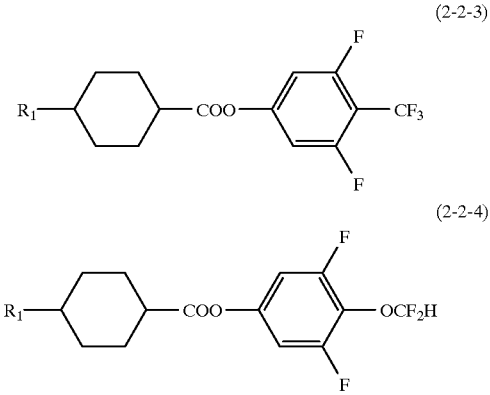

where $R_1$, is as described above.

Among these compounds, compounds represented by the general formula (2-2-1) are particularly preferable.

As the compounds represented by the general formula (2-3) of the present invention, compounds represented by the following general formulas (2-3-1) through (2-3-12) are preferably used.

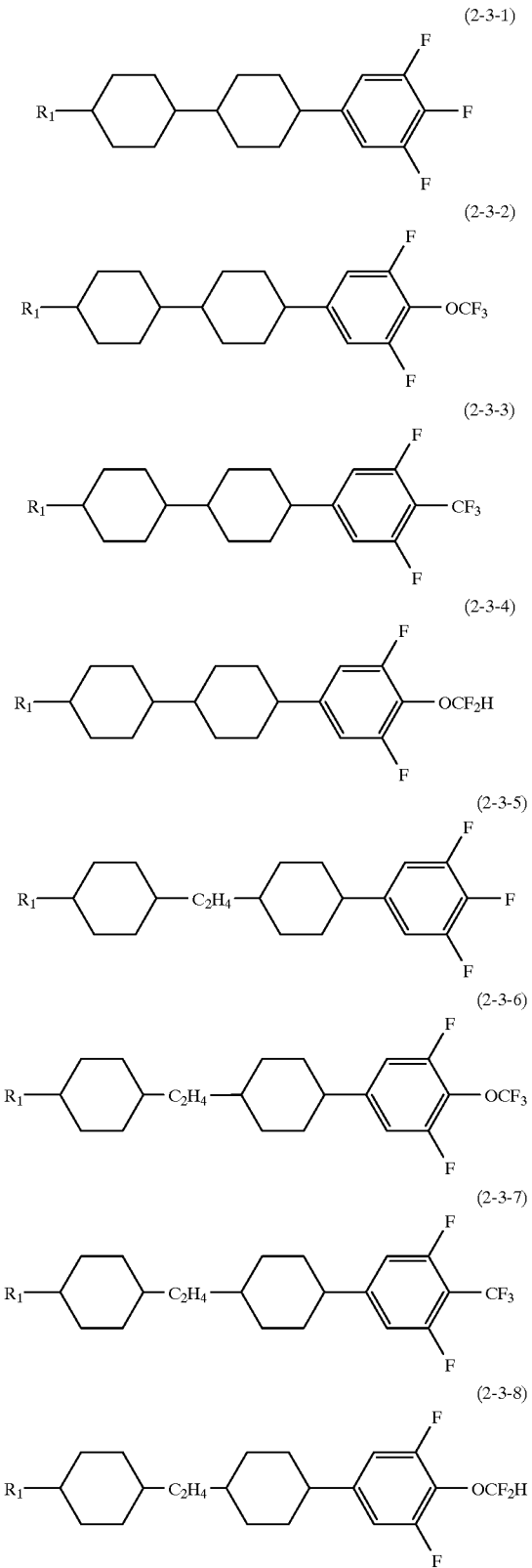

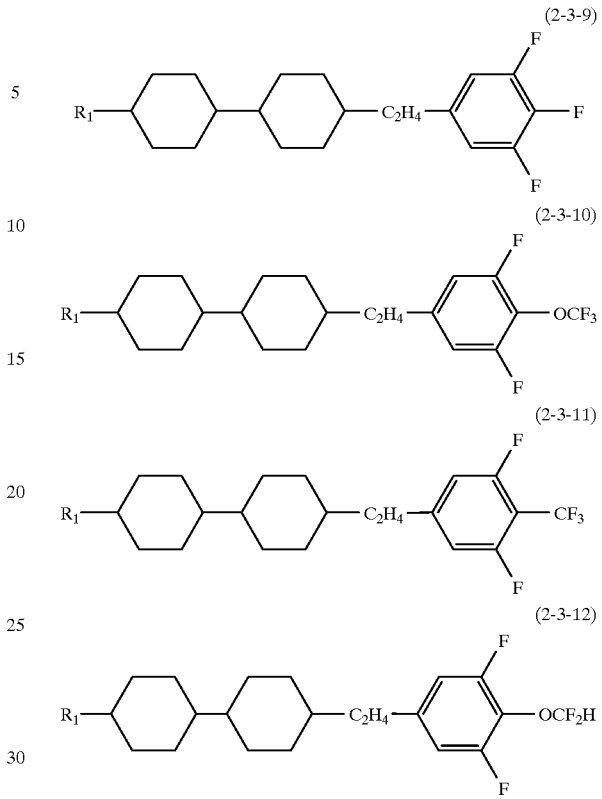

where $R_1$ is as described above.

Among these compounds, compounds represented by the general formulas (2-3-1), (2-3-5), and (2-3-9) are particularly preferable.

As the compounds represented by the general formula (2-4) of the present invention, compounds represented by the following general formulas (2-4-1) through (2-4-4) are preferably used.

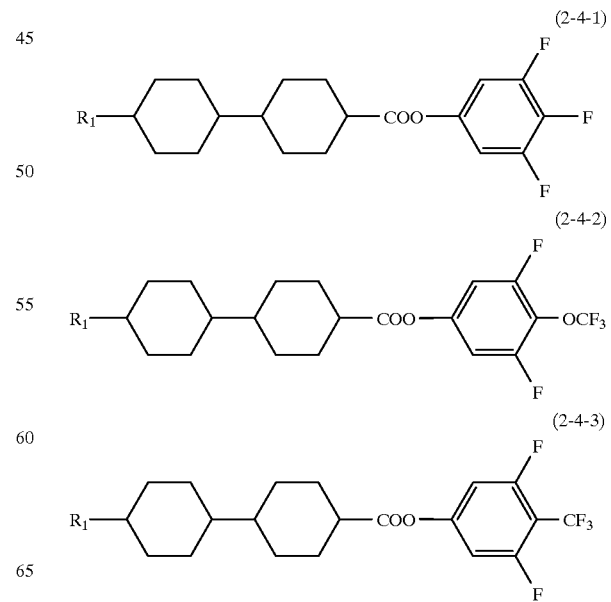

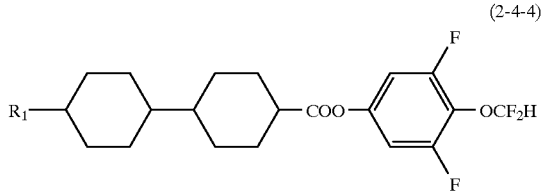
(2-4-4)

where R₁ is as described above.

Among these compounds, compounds represented by the general formula (2-4-1) are particularly preferable.

As the compounds represented by the general formula (2-5) of the present invention, compounds represented by the following general formulas (2-5-1) through (2-5-8) are preferably used.

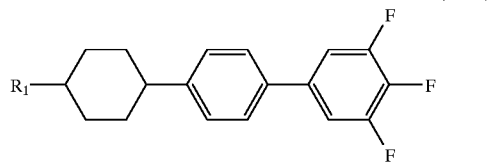
(2-5-1)

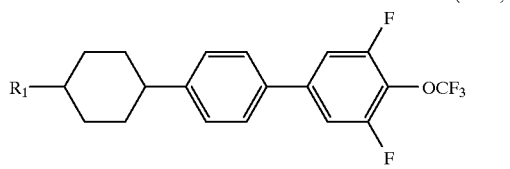
(2-5-2)

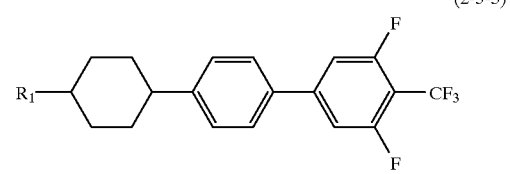
(2-5-3)

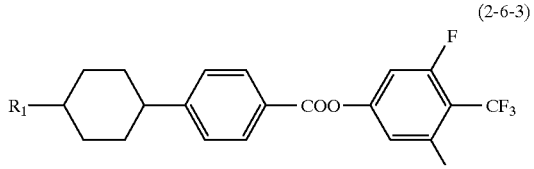
(2-5-4)

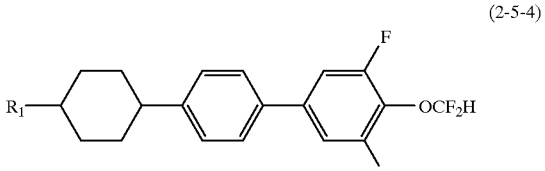
(2-5-5)

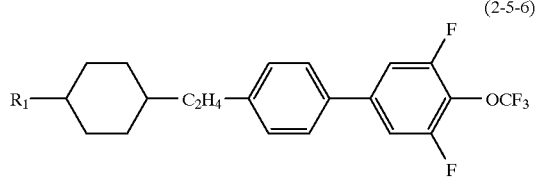
(2-5-6)

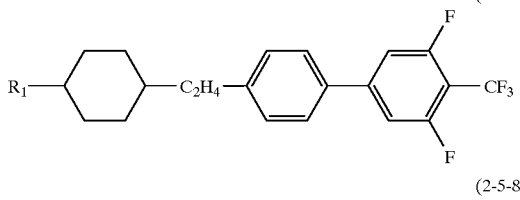
(2-5-7)

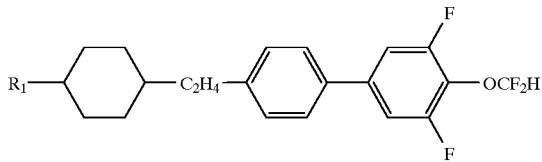
(2-5-8)

where R₁ is as described above.

Among these compounds, compounds represented by the general formulas (2-5-1) and (2-5-5) are particularly preferable.

As the compounds represented by the general formula (2-6) of the present invention, compounds represented by the following general formulas (2-6-1) through (2-6-4) are preferably used.

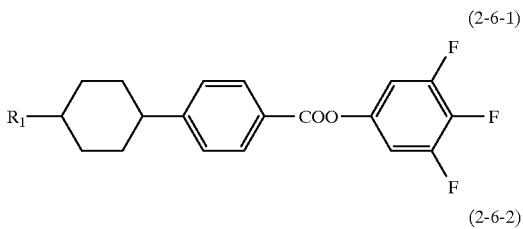
(2-6-1)

(2-6-2)

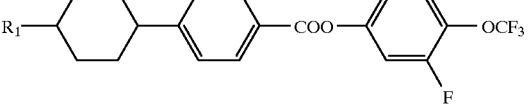
(2-6-3)

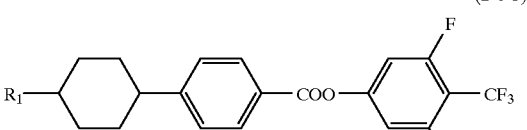
(2-6-3)

(2-6-4)

where R₁ is as described above.

Among these compounds, compounds represented by the general formula (2-6-1) are particularly preferable.

As the compounds represented by the general formula (2-7) of the present invention, compounds represented by the following general formulas (2-7-1) through (2-7-4) are preferably used.

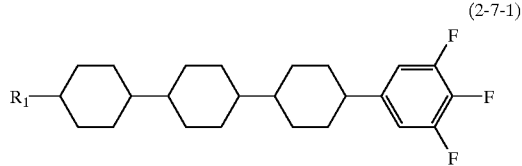
(2-7-1)

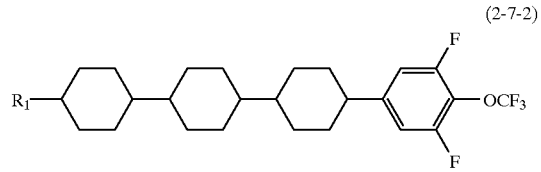
(2-7-2)

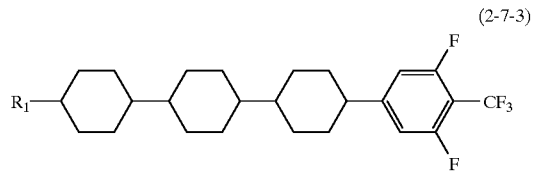
(2-7-3)

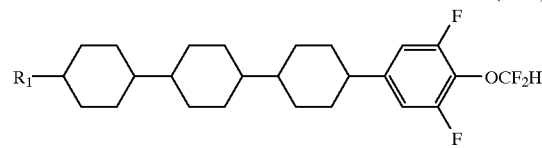
(2-7-4)

where $R_1$ is as described above.

Among these compounds, compounds represented by the general formula (2-7-1) are particularly preferable.

As the compounds represented by the general formula (2-8) of the present invention, compounds represented by the following general formulas (2-8-1) through (2-8-8) are preferably used.

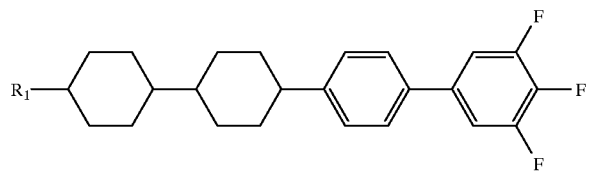
(2-8-1)

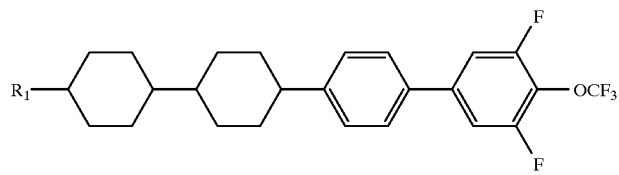
(2-8-2)

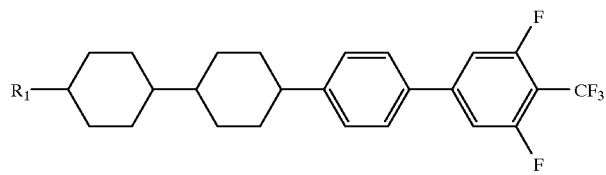
(2-8-3)

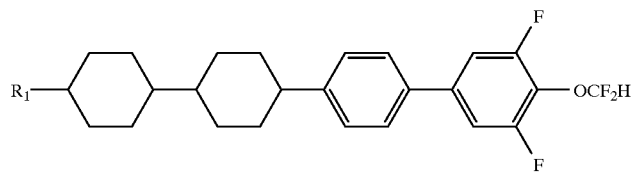
(2-8-4)

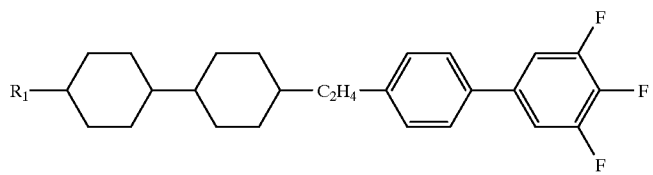
(2-8-5)
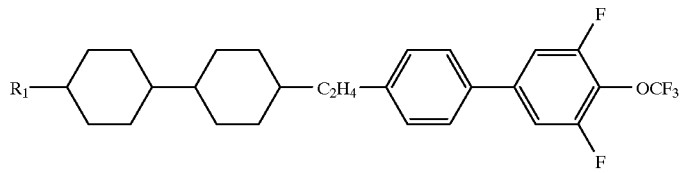
(2-8-6)
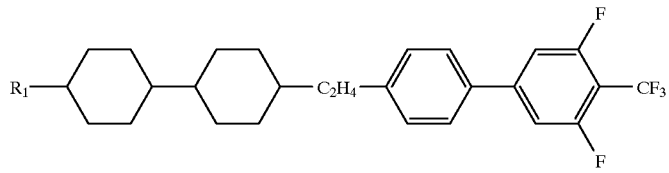
(2-8-7)
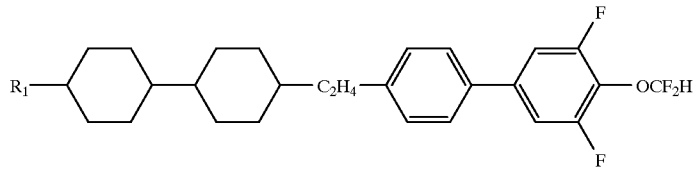
(2-8-8)
where $R_1$ is as described above.
Among these compounds, compounds represented by the general formulas (2-8-1) and (2-8-5) are particularly preferably used.
As the compounds represented by the general formula (3-1) of the present invention, compounds represented by the following general formulas (3-1-1) through (3-1-24) are preferably used.
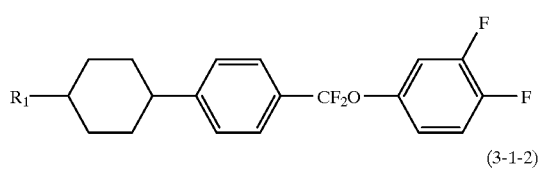
(3-1-1)
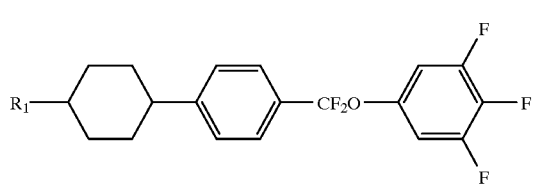
(3-1-2)
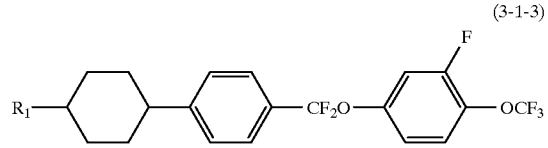
(3-1-3)
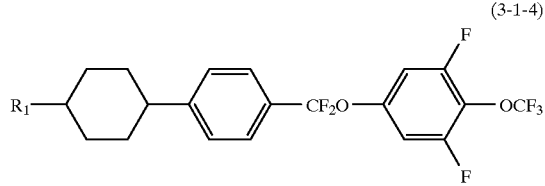
(3-1-4)
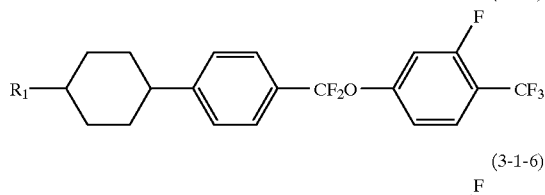
(3-1-5)
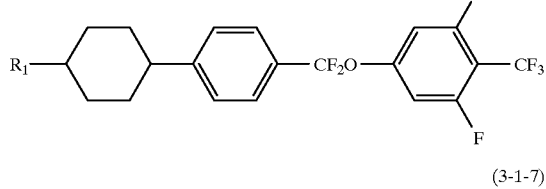
(3-1-6)
(3-1-7)

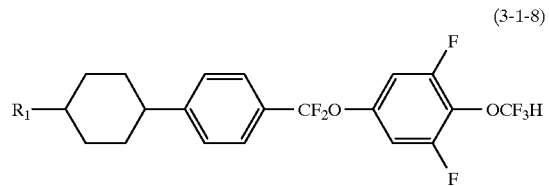
(3-1-8)
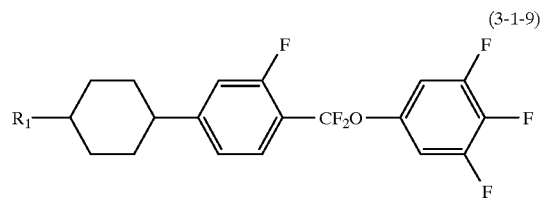
(3-1-9)
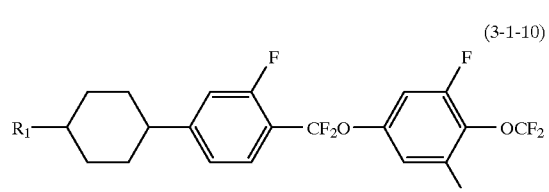
(3-1-10)
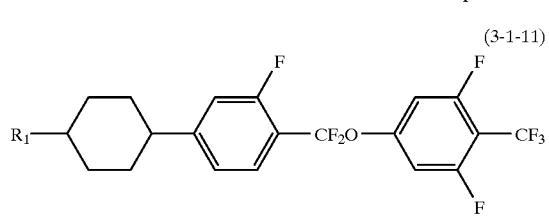
(3-1-11)
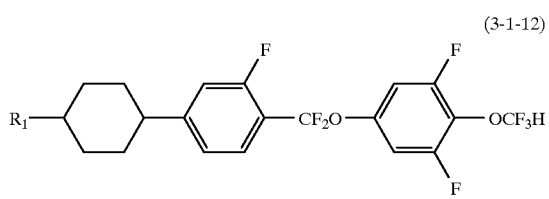
(3-1-12)
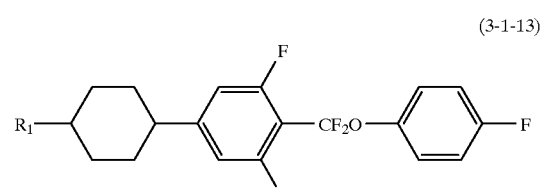
(3-1-13)
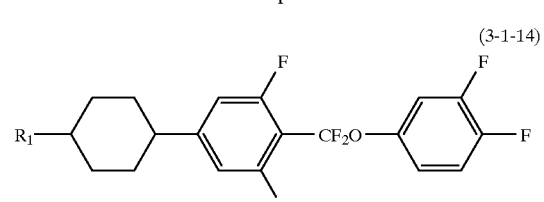
(3-1-14)
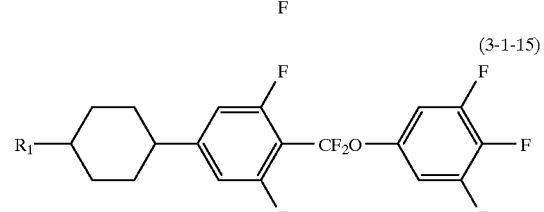
(3-1-15)
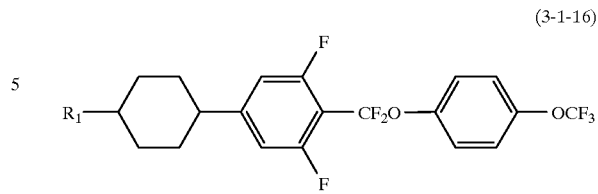
(3-1-16)
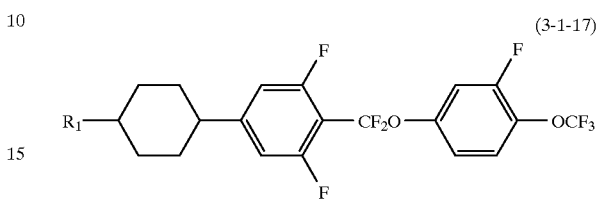
(3-1-17)
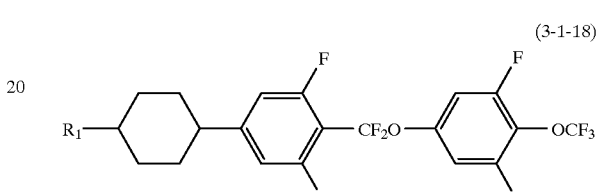
(3-1-18)
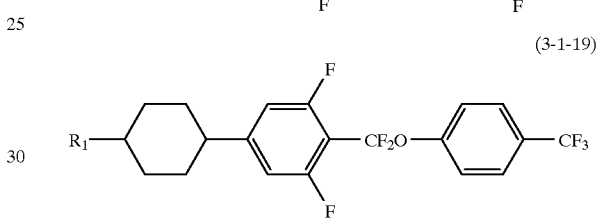
(3-1-19)
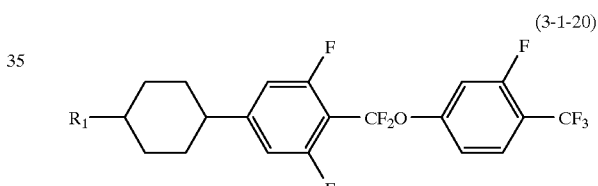
(3-1-20)
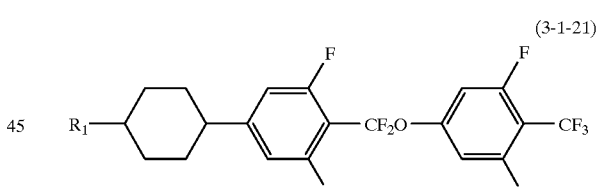
(3-1-21)
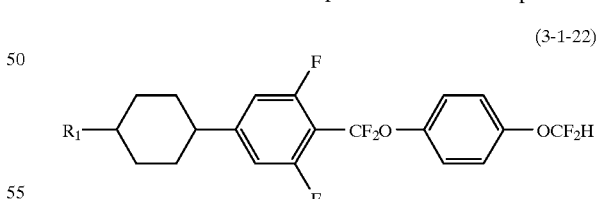
(3-1-22)
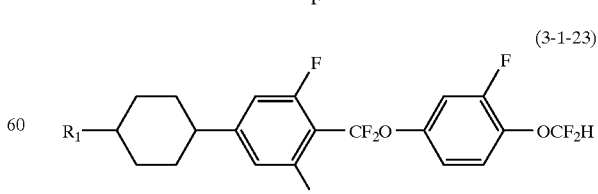
(3-1-23)

(3-1-24)
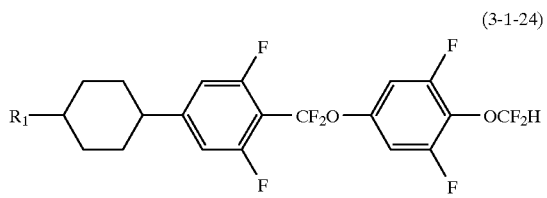
where $R_1$ is as described above.
Among these compounds, compounds represented by the general formulas (3-1-2), (3-1-3), (3-1-9), (3-1-14), (3-1-15), and (3-1-17) are particularly preferable.
As the compounds represented by the general formula (3-2) of the present invention, compounds represented by the following general formulas (3-2-1) through (3-2-23) are preferably used.
(3-2-1)
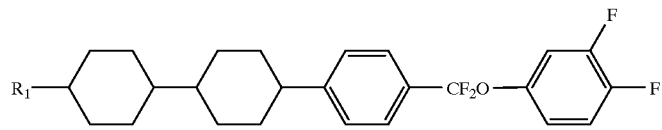
(3-2-2)
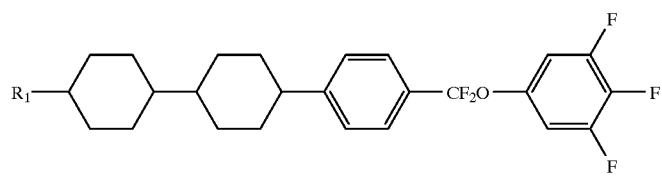
(3-2-3)
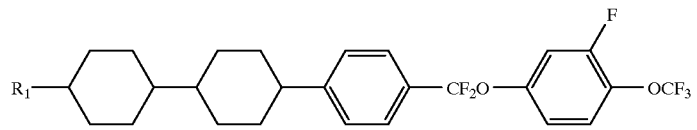
(3-2-4)
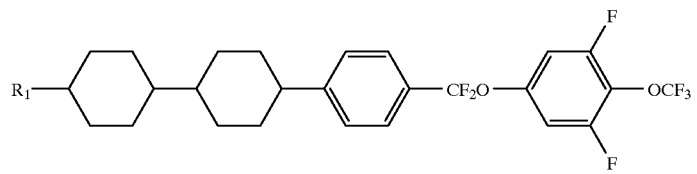
(3-2-5)
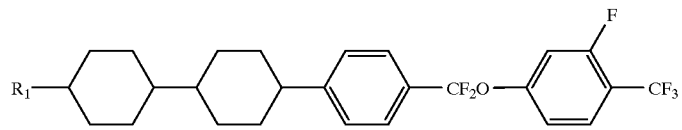
(3-2-6)
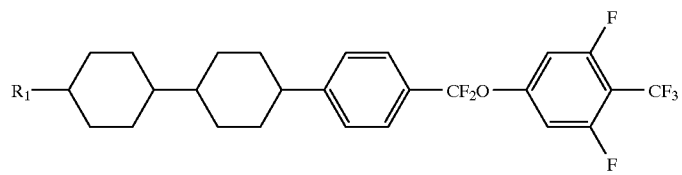
(3-2-7)
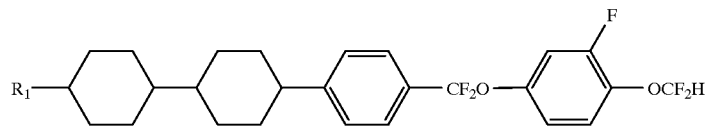

-continued
(3-2-8)
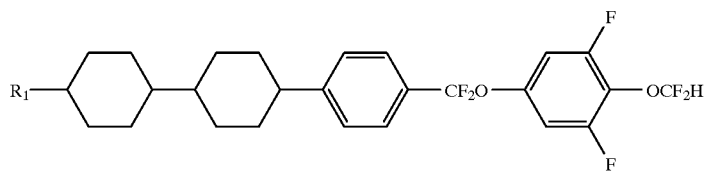
(3-2-9)
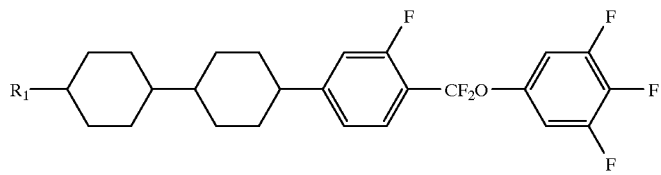
(3-2-10)
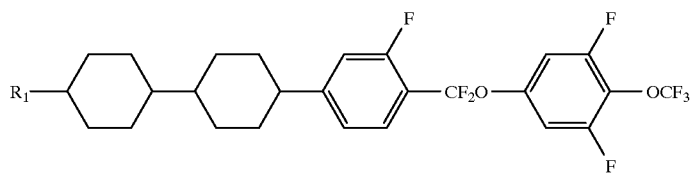
(3-2-11)
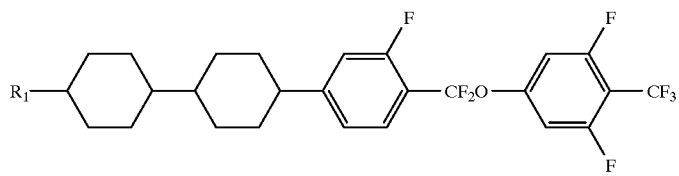
(3-2-12)
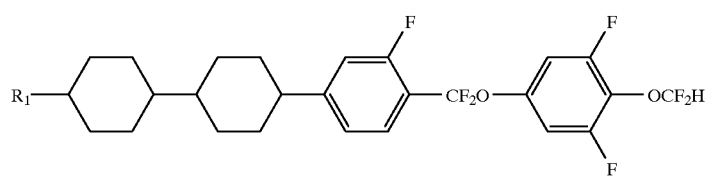
(3-2-13)
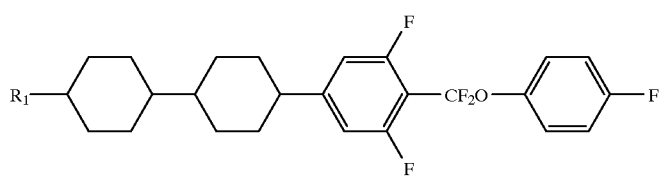
(3-2-14)
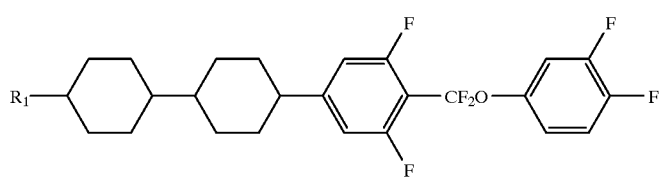
(3-2-15)
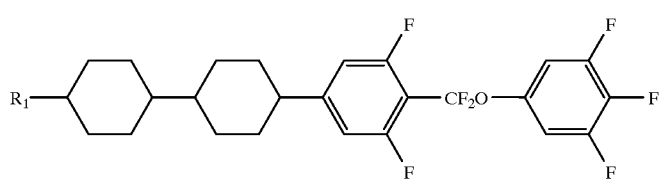

-continued
(3-2-16)
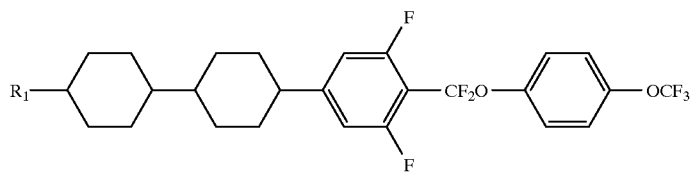
(3-2-17)
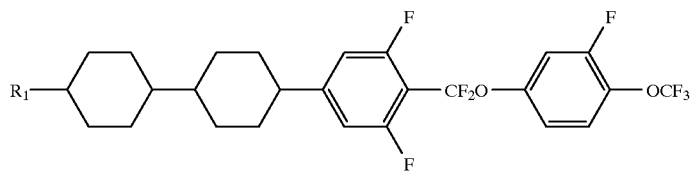
(3-2-18)
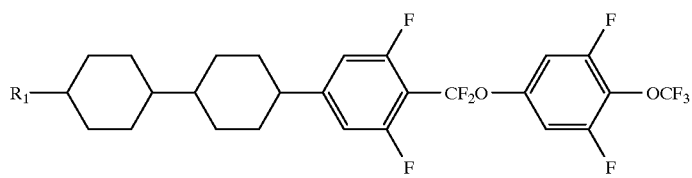
(3-2-19)
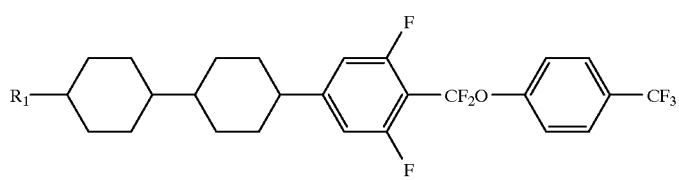
(3-2-20)
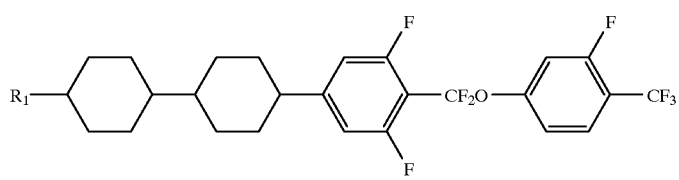
(3-2-21)
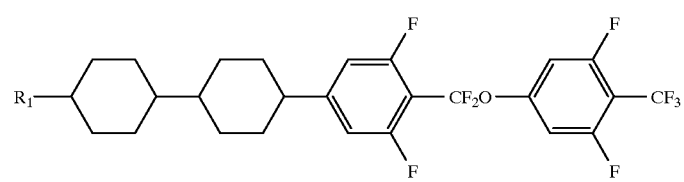
(3-2-22)
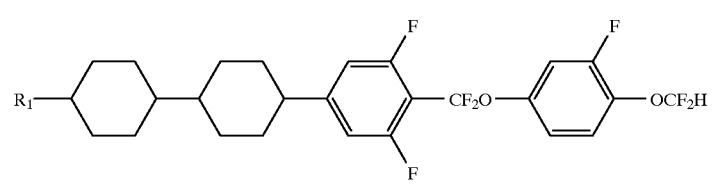
(3-2-23)
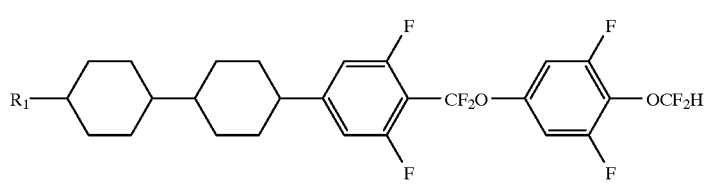
where $R_1$ is as described above.

Among these compounds, compounds represented by the general formulas (3-2-2), (3-2-3), (3-2-9), (3-2-14), (3-2-15), and (3-2-17) are particularly preferable.

The compounds represented by the general formula (1-1) of the present invention have a large anisotropy of inductivity, excellent thermal and optical stability, small elastic modulus, and low upper limit of the nematic phase (NI point). Therefore, the compounds represented by the general formula (1-1) of the present invention play a role of considerably lowering the threshold voltage of a liquid crystal composition for active matrix type display elements, and are useful for controlling the NI point of the liquid crystal composition.

The compounds represented by the general formula (1-2) of the present invention have a large anisotropy of inductivity, excellent thermal and optical stability, and an NI point higher than that of the compounds represented by the general formula (1-1) of the present invention. Therefore, the compounds represented by the general formula (1-2) of the present invention play a role of considerably lowering the threshold voltage of a liquid crystal composition for active matrix type display elements, and are useful for elevating the NI point of the liquid crystal composition.

The amount of the first component used in the liquid crystal composition according to the present invention relative to the total amount of the composition is preferably 3 to 70 percent by weight, and more preferably 5 to 55 percent by weight. If the amount of the first component used in the composition is less than 3 percent by weight, lowering the threshold voltage, which is an object of the present invention, tends to be difficult. If the amount of the first component exceeds 70 percent by weight, the lower temperature limit of the nematic phase tends to increase.

The compounds represented by the general formulas (2-1) and (2-2) of the present invention have a relatively large $\Delta\epsilon$, a small elastic modulus, excellent thermal and optical stability, and a low NI point. Therefore, the compounds represented by the general formulas (2-1) and (2-2) of the present invention play a role of controlling the threshold voltage of a liquid crystal composition for active matrix type display elements, and are useful for controlling the NI point of the liquid crystal composition.

The compounds represented by the general formulas (2-3) through (2-6) of the present invention have a relatively large $\Delta\epsilon$, excellent thermal and optical stability, and an NI point higher than that of the compounds represented by the general formulas (2-1) and (2-2). Therefore, the compounds represented by the general formulas (2-3) through (2-6) of the present invention play a role of controlling the threshold voltage of a liquid crystal composition for active matrix type display elements, and are useful for elevating the NI point of the liquid crystal composition.

The compounds represented by the general formulas (2-7) and (2-8) of the present invention have a relatively large $\Delta\epsilon$, excellent thermal and optical stability, and an NI point considerably higher than that of the compounds represented by the general formulas (2-1) through (2-6). Therefore, the compounds represented by the general formulas (2-7) and (2-8) of the present invention play a role of controlling the threshold voltage of a liquid crystal composition for active matrix type display elements, and are useful for controlling the NI point of the liquid crystal composition.

The amount of the second component used in the liquid crystal composition according to the present invention relative to the total amount of the composition is preferably 27 to 97 percent by weight, and more preferably 35 to 85 percent by weight. If the amount of the second component used in the composition is less than 27 percent by weight, the lower temperature limit of the nematic phase tends to increase. If the amount of the second component exceeds 97 percent by weight, lowering the threshold voltage, which is an object of the present invention, tends to be difficult.

The amount of the compounds represented by the general formulas (2-1) and (2-2), which are used as the second component in the liquid crystal composition according to the present invention, is preferably 20 percent by weight or less relative to the total amount of the composition, and more preferably 15 percent by weight or less. If the amount of the compounds represented by the general formulas (2-1) and (2-2) is larger than 20 percent by weight, the NI point tends to be lowered.

The amount of the compounds represented by the general formulas (2-3) through (2-6), which are used as the second component in the liquid crystal composition according to the present invention, is preferably 90 percent by weight or less relative to the total amount of the composition, and more preferably 80 percent by weight or less. If the amount of the compounds represented by the general formulas (2-3) through (2-6) is larger than 90 percent by weight, lowering the threshold voltage, which is an object of the present invention, tends to be difficult.

The amount of the compounds represented by the general formulas (2-7) and (2-8), which are used as the second component in the liquid crystal composition according to the present invention, is preferably 20 percent by weight or less relative to the total amount of the composition, and more preferably 15 percent by weight or less. If the amount of the compounds represented by the general formulas (2-7) and (2-8) is larger than 20 percent by weight, the lower temperature limit of the nematic phase tends to be elevated.

The compounds represented by the general formulas (3-1) and (3-2) of the present invention have a large anisotropy of inductivity, excellent thermal and optical stability, and a large anisotropy of refractive index. Therefore, the compounds represented by the general formulas (3-1) and (3-2) of the present invention play a role of lowering the threshold voltage of a liquid crystal composition for active matrix type display elements, and are useful for increasing or controlling the anisotropy of refractive index of the liquid crystal composition.

The amount of the third component used in the liquid crystal composition according to the present invention relative to the total amount of the composition is preferably 3 to 50 percent by weight, and more preferably 10 to 40 percent by weight. If the amount of the third component used in the composition is less than 3 percent by weight, lowering the threshold voltage, which is an object of the present invention, tends to be difficult; and if the amount of the first component exceeds 70 percent by weight, the anisotropy of refractive index of the liquid crystal composition tends to increase.

In the liquid crystal composition of the present invention, liquid crystal compounds other than those represented by general formulas indicated above may be used in combination within the scope of the object of the present invention.

Liquid crystal compositions used in the present invention may be prepared by methods known to those skilled in the art. In general, the methods involve mixing various compounds, and dissolving them in each other.

In the liquid crystal composition of the present invention, a chiral dopant may be added for inducing the spiral structure of liquid crystal molecules, and for controlling desired twist angles.

The liquid crystal composition of the present invention can be used as a guest-host mode liquid crystal composition by the addition of merocyanine, styryl, azo, azomethine, azoxy, quinophthalone, anthraquinone, or tetrazine dichromatic dyes; and can also be used for producing a polymer dispersion type liquid crystal display element, and as double refraction controlling mode and dynamic scattering mode liquid crystal compositions.

The present invention will be described below in further detail in reference to preferred embodiments. However, the embodiments described below should not be construed to limit the present invention. All composition ratios indicated in examples and comparative examples are in percentage by weight. Compounds used in examples and comparative examples are represented by symbols based on definitions listed in Table 1.

TABLE 1

Manner for describing compounds with codes
R—($A_1$)—$Z_1$—$Z_n$—($A_n$)—X

| 1) Left end group R— | Code |
|---|---|
| $C_nH_{2n+1}$— | n- |
| $CH_3$—O—$CH_2$— | 101- |

2) Cyclic structure

| —($A_1$)—, —($A_n$)— | Code |
|---|---|
| hexane ring | H |
| benzene ring | B |
| fluorobenzene ring | B(F) |
| difluorobenzene ring | B(F,F) |

3) Bond group —$Z_1$—, —$Z_n$—

| | Code |
|---|---|
| —$C_2H_4$— | 2 |
| —COO— | E |
| —$CF_2$O— | CF2O |

4) Right end group —X

| | Code |
|---|---|
| —F | —F |
| —$OCF_2H$ | —OF2H |
| —$OCF_3$ | —OCF3 |
| —$CF_3$ | —CF3 |

5) Description examples

Example 1  3-H2B(F,F)B(F)—F

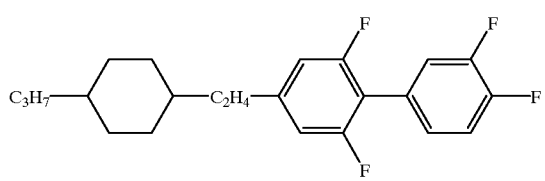

TABLE 1-continued

Manner for describing compounds with codes
R—($A_1$)—$Z_1$—$Z_n$—($A_n$)—X

Example 2  3-HB(F,F)CF2OB(F,F)—F

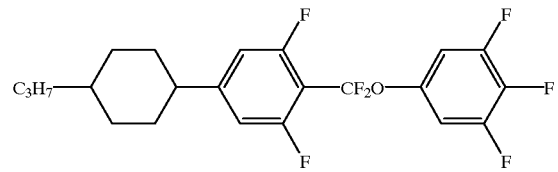

Property data of liquid crystal compositions are shown in terms of $T_{NI}$ representing the upper temperature limit of the nematic liquid crystal phase, $T_C$, representing the lower temperature limit of the nematic liquid crystal phase, viscosity at 20° C. ($\eta$), anisotropy of refractive index at 25° C. and 589 nm ($\Delta n$), and threshold voltage at 20° C. (Vth). The measurement of voltage holding rate (VHR) was conducted at 25° C. according to the area method. $T_C$ was determined by the liquid crystal phase being held for 30 days in a freezer maintained at 0° C., −10° C., −20° C. and −30° C.

COMPARATIVE EXAMPLE 1

A composition disclosed in Application Example 2 of Japanese Patent Application Laid-open No. 2-233626 was prepared.

| 3-HHB(F,F)-F | 15.0% |
|---|---|
| 2-HHB(F)-F | 28.4% |
| 3-HHB(F)-F | 28.3% |
| 5-HHB(F)-F | 28.3% |

The properties of the above composition were as follows:
$T_{NI}$=110.7° C.
$T_C$<0° C.
$\eta$=25.0 mPa·s
$\Delta n$=0.077
Vth=2.32 V
VHR=98.8%

The above composition has the disadvantages of high Vth and high $T_C$ point.

COMPARATIVE EXAMPLE 2

A composition disclosed in Example 1 of WO94/03558 was prepared.

| 7-HB(F,F)-F | 10.0% |
|---|---|
| 2-HHB(F,F)-F | 25.0% |
| 3-HHB(F,F)-F | 35.0% |
| 5-HHB(F,F)-F | 18.0% |
| 7-HB(F)-F | 12.0% |

The properties of the above composition were as follows:
$T_{NI}$=42.9° C.
$T_C$<0° C.
$\eta$=22.2 mPa·s
$\Delta n$=0.059
Vth=1.07 V
VHR=98.7%

The above composition has the disadvantages of low NI point and high $T_C$ point.

COMPARATIVE EXAMPLE 3

A composition disclosed in Example 4 of W094/03558 was prepared.

| | |
|---|---|
| 2-HHB(F,F)-F | 10.0% |
| 3-HHB(F,F)-F | 10.0% |
| 5-HHB(F,F)-F | 10.0% |
| 5-H2B(F)-F | 10.0% |
| 5-HEB-F | 7.5% |
| 7-HEB-F | 7.5% |
| 2-HHB(F)-F | 11.7% |
| 3-HHB(F)-F | 11.7% |
| 5-HHB(F)-F | 11.6% |
| 3-HHB-F | 5.0% |
| 5-HHEB-F | 2.5% |
| 7-HHEB-F | 2.5% |

The properties of the above composition were as follows:
$T_{NI}$=71.3° C.
$T_C$<-20° C.
η=19.2 mpa·s
Δn=0.070
Vth=1.77 V
VHR=98.2%

The above composition has the disadvantage of low Vth.

EXAMPLE 1

There was prepared a liquid crystal composition comprising as a first component:

| | |
|---|---|
| 2-HHCF2OB(F,F)-F | 4.0% |
| 3-HHCF2OB(F,F)-F | 4.0% |
| 4-HHCF2OB(F,F)-F | 4.0% |
| 5-HHCF2OB(F,F)-F | 4.0% |
| 2-H2HCF2OB(F,F)-F | 4.0% |
| 3-H2HCF2OB(F,F)-F | 4.0% |
| 4-H2HCF2OB(F,F)-F | 4.0% |
| 5-H2HCF2OB(F,F)-F | 4.0% |
| and as a second component: | |
| 3-H2HB(F,F)-F | 6.0% |
| 3-HBB(F,F)-F | 15.0% |
| 3-HBB(F,F)-F | 10.0% |
| 5-HBB(F,F)-F | 15.0% |
| 2-HBEB(F,F)-F | 2.0% |
| 3-HBEB(F,F)-F | 2.0% |
| 4-HBEB(F,F)-F | 2.0% |
| 3-HHEB(F,F)-F | 10.0% |
| 4-HHEB(F,F)-F | 3.0% |
| 5-HHEB(F,F)-F | 3.0% |

The properties of the above composition were as follows:
$T_{NI}$=81.8° C.
$T_C$<-20° C.
η=28.3 mpa·s
Δn=0.091
Vth=1.40 V
VHR=98.5%

The above composition has features of low Vth, high $T_{NI}$ point, and low $T_C$ point.

EXAMPLE 2

There was prepared a liquid crystal composition comprising as a first component:

| | |
|---|---|
| 5-HCF2OB(F,F)-F | 11.0% |
| 7-HCF2OB(F,F)-F | 10.0% |
| 2-HHCF2OB(F,F)-F | 5.0% |
| 3-HHCF2OB(F,F)-F | 5.0% |
| 4-HHCF2OB(F,F)-F | 5.0% |
| 5-HHCF2OB(F,F)-F | 5.0% |
| 2-H2HCF2OB(F,F)-F | 5.0% |
| 3-H2HCF2OB(F,F)-F | 5.0% |
| and as a second component: | |
| 3-HH2B(F,F)-F | 14.0% |
| 5-HH2B(F,F)-F | 8.0% |
| 3-H2BB(F,F)-F | 18.0% |
| 2-HHBB(F,F)-F | 3.0% |
| 3-HHBB(F,F)-F | 3.0% |
| 3-HH2BB(F,F)-F | 3.0% |

The properties of the above composition were as follows:
$T_{NI}$=72.0° C.
$T_C$<-20° C.
η=25.7 mpa·s
Δn=0.083
Vth=1.48 V
VHR=98.8%

The above composition has features of low Vth, high $T_{NI}$ point, and low $T_C$ point.

EXAMPLE 3

There was prepared a liquid crystal composition comprising as a first component:

| | |
|---|---|
| 3-HHCF2OB(F)-OCF3 | 6.0% |
| 4-HHCF2OB(F)-OCF3 | 6.0% |
| as a second component: | |
| 4-H2HB(F,F)-F | 10.0% |
| 5-H2HB(F,F)-F | 10.0% |
| 3-HHB(F,F)-F | 10.0% |
| 4-HHB(F,F)-F | 5.0% |
| 3-HH2B(F,F)-F | 10.0% |
| 3-HBB(F,F)-F | 3.0% |
| 2-HHBB(F,F)-F | 2.0% |
| 3-HHBB(F,F)-F | 2.0% |
| 4-HHBB(F,F)-F | 2.0% |
| 5-HHBB(F,F)-F | 2.0% |
| 3-HH2BB(F,F)-F | 2.0% |
| 4-HH2BB(F,F)-F | 2.0% |
| and as a third component: | |
| 3-HB(F,F)CF2OB(F,F)-F | 10.0% |
| 4-HB(F,F)CF2OB(F,F)-F | 10.0% |
| 5-HB(F,F)CF2OB(F,F)-F | 8.0% |

The properties of the above composition were as follows:
$T_{NI}$=76.5° C.
$T_C$<-20° C.
η=31.2 mpa·s
Δn=0.084
Vth=1.30 V
VHR=98.7%

The above composition has features of low Vth, high $T_{NI}$, point, and low $T_C$ point.

EXAMPLE 4

There was prepared a liquid crystal composition comprising as a first component:

| | |
|---|---|
| 3-HHCF2OB(F)-F | 2.0% |
| 3-H2HCF2OB(F)-F | 2.0% |
| 3-H2HCF2OB(F)-OCF3 | 2.0% |
| 2-HHCF2OB(F,F)-F | 5.0% |
| 3-HHCF2OB(F,F)-F | 5.0% |
| 4-HHCF2OB(F,F)-F | 5.0% |
| 5-HHCF2OB(F,F)-F | 5.0% |
| as a second component: | |
| | |
| 7-HB(F,F)-F | 9.0% |
| 3-H2HB(F,F)-F | 6.0% |
| 3-HHB(F,F)-F | 10.0% |
| 4-HHB(F,F)-F | 5.0% |
| 3-HH2B(F,F)-F | 7.0% |
| 3-HBB(F,F)-F | 15.0% |
| 5-HEB(F,F)-F | 6.0% |
| and as a third component: | |
| | |
| 2-HHB(F,F)CF2OB(F,F)-F | 4.0% |
| 3-HHB(F,F)CF2OB(F,F)-F | 4.0% |
| 4-HHB(F,F)CF2OB(F,F)-F | 4.0% |
| 5-HHB(F,F)CF2OB(F,F)-F | 4.0% |

The properties of the above composition were as follows:
$T_{NI}$=71.2° C.
$T_C$<-10° C.
η=26.2 mpa·s
Δn=0.080
Vth=1.45 V
VHR=98.6%

The above composition has features of low Vth, high $T_{NI}$ point, and low $T_C$ point.

EXAMPLE 5

There was prepared a liquid crystal composition comprising as a first component:

| | |
|---|---|
| 5-HCF2OB(F)-F | 2.0% |
| 5-HCF2OB(F)-OCF3 | 2.0% |
| 2-HHCF2OB(F,F)-F | 5.0% |
| 3-HHCF2OB(F,F)-F | 5.0% |
| 4-HHCF2OB(F,F)-F | 5.0% |
| 5-HHCF2OB(F,F)-F | 5.0% |
| as a second component: | |
| | |
| 7-HB(F,F)-F | 8.0% |
| 3-H2HB(F,F)-F | 7.0% |
| 3-HHB(F,F)-F | 10.0% |
| 4-HHB(F,F)-F | 5.0% |
| 2-HHBB(F,F)-F | 4.0% |
| 3-HHBB(F,F)-F | 4.0% |
| and as a third component: | |
| | |
| 3-HHBCF2OB(F,F)-F | 2.0% |
| 3-HHBCF2OB(F)-OCF3 | 2.0% |
| 3-HBCF2OB(F)-OCF3 | 11.0% |
| 4-HBCF2OB(F)-OCF3 | 11.0% |
| 5-HBCF2OB(F)-OCF3 | 12.0% |

The properties of the above composition were as follows:
$T_{NI}$=70.4° C.
$T_C$<-20° C.
η=23.8 mpa·s
Δn=0.082
Vth=1.48 V
VHR=98.9%

The above composition has features of low Vth, high $T_{NI}$ point, and low $T_C$ point.

EXAMPLE 6

There was prepared a liquid crystal composition comprising as a first component:

| | |
|---|---|
| 2-HHCF2OB(F,F)-F | 4.0% |
| 3-HHCF2OB(F,F)-F | 4.0% |
| 4-HHCF2OB(F,F)-F | 4.0% |
| 5-HHCF2OB(F,F)-F | 4.0% |
| as a second component: | |
| | |
| 7-HB(F,F)-F | 12.0% |
| 3-HBB(F,F)-F | 29.0% |
| 2-HBEB(F,F)-F | 3.0% |
| 3-HBEB(F,F)-F | 5.0% |
| 5-HBEB(F,F)-F | 3.0% |
| 3-HHEB(F,F)-F | 10.0% |
| 4-HHEB(F,F)-F | 3.0% |
| 5-HHEB(F,F)-F | 5.0% |
| 2-HHBB(F,F)-F | 4.0% |
| and as a third component: | |
| | |
| 3-HB(F,F)CF2OB(F)-F | 2.0% |
| 3-HB(F,F)CF2OB(F)-OCF3 | 2.0% |
| 3-HHB(F)CF2OB(F,F)-F | 2.0% |
| 3-HHB(F,F)CF2OB(F)-OCF3 | 2.0% |
| 3-HHB(F,F)CF2OB(F)-F | 2.0% |

The properties of the above composition were as follows:
$T_{NI}$=70.0° C.
$T_C$<-30° C.
η=34.0 mpa·s
Δn=0.094
Vth=1.20 V
VHR=98.7%

The above composition has features of low Vth, high $T_{NI}$ point, and low $T_C$ point.

EXAMPLE 7

There was prepared a liquid crystal composition comprising as a first component:

| | |
|---|---|
| 2-HHCF2OB(F,F)-F | 4.0% |
| 3-HHCF2OB(F,F)-F | 4.0% |
| 4-HHCF2OB(F,F)-F | 4.0% |
| 5-HHCF2OB(F,F)-F | 4.0% |
| 2-H2HCF2OB(F,F)-F | 4.0% |
| 3-H2HCF2OB(F,F)-F | 4.0% |
| 4-H2HCF2OB(F,F)-F | 4.0% |
| 5-H2HCF2OB(F,F)-F | 4.0% |
| as a second component: | |
| | |
| 3-HBB(F,F)-F | 30.0% |
| 3-HHBB(F,F)-F | 3.0% |
| 2-HHHB(F,F)-F | 2.0% |
| 3-HHHB(F,F)-F | 2.0% |
| 4-HHHB(F,F)-F | 2.0% |
| and as a third component: | |
| | |
| 2-HBCF2OB(F,F)-F | 4.0% |
| 3-HBCF2OB(F,F)-F | 4.0% |
| 4-HBCF2OB(F,F)-F | 4.0% |
| 5-HBCF2OB(F,F)-F | 4.0% |
| 2-HB(F)CF2OB(F,F)-F | 4.0% |
| 3-HB(F)CF2OB(F,F)-F | 4.0% |
| 4-HB(F)CF2OB(F,F)-F | 5.0% |

The properties of the above composition were as follows:
$T_{NI}$=73.8° C.
$T_C$<-20° C.
η=36.0 mPa·s
Δn=0.105
Vth=1.38 V
VHR=98.7%

The above composition has features of low Vth, high $T_{NI}$ point, and low $T_C$ point.

EXAMPLE 8

There was prepared a liquid crystal composition comprising as a first component:

| | |
|---|---|
| 3-HHCF2OB(F,F)-F | 5.0% |
| and as a second component: | |
| 7-HB(F,F)-F | 7.0% |
| 3-H2HB(F,F)-F | 8.0% |
| 4-H2HB(F,F)-F | 8.0% |
| 3-HBB(F,F)-F | 29.0% |
| 5-HBB(F,F)-F | 4.0% |
| 2-HBEB(F,F)-F | 3.0% |
| 3-HBEB(F,F)-F | 5.0% |
| 5-HBEB(F,F)-F | 3.0% |
| 3-HHEB(F,F)-F | 10.0% |
| 4-HHEB(F,F)-F | 3.0% |
| 5-HHEB(F,F)-F | 5.0% |
| 2-HHBB(F,F)-F | 5.0% |
| 3-HHBB(F,F)-F | 5.0% |

The properties of the above composition were as follows:

$T_{NI}$=76.9° C.
$T_C$<-30° C.
η=34.0 mpa·s
Δn=0.094
Vth=1.30 V
VHR=98.7%

EXAMPLE 9

There was prepared a liquid crystal composition comprising as a first component:

| | |
|---|---|
| 2-HHCF2OB(F,F)-CF3 | 2.0% |
| 3-HHCF2OB(F,F)-CF3 | 2.0% |
| 2-HHCF2OB(F,F)-OCF2H | 2.0% |
| 3-HHCF2OB(F,F)-OCF2H | 2.0% |
| 4-HHCF2OB(F,F)-F | 4.0% |
| 5-HHCF2OB(F,F)-F | 4.0% |
| 2-H2HCF2OB(F,F)-F | 4.0% |
| 3-H2HCF2OB(F,F)-F | 4.0% |
| 4-H2HCF2OB(F,F)-F | 4.0% |
| 5-H2HCF2OB(F,F)-F | 4.0% |
| as a second component: | |
| 2-HBB(F,F)-CF3 | 2.0% |
| 3-HBB(F,F)-CF3 | 2.0% |
| 2-HBB(F,F)-OCF2H | 2.0% |
| 3-HBB(F,F)-OCF2H | 2.0% |
| 2-HBB(F,F)-OCF3 | 2.0% |
| 3-HBB(F,F)-OCF3 | 2.0% |
| 3-HBB(F,F)-F | 18.0% |
| 3-HHBB(F,F)-F | 3.0% |
| 2-HHHB(F,F)-F | 2.0% |
| 3-HHHB(F,F)-F | 2.0% |
| 4-HHHB(F,F)-F | 2.0% |
| and as a third component: | |
| 2-HBCF2OB(F,F)-CF3 | 2.0% |
| 3-HBCF2OB(F,F)-CF3 | 2.0% |
| 2-HBCF2OB(F,F)-OCF2H | 2.0% |
| 3-HBCF2OB(F,F)-OCF2H | 2.0% |
| 4-HBCF2OB(F,F)-F | 4.0% |
| 5-HBCF2OB(F,F)-F | 4.0% |
| 2-HB(F)CF2OB(F,F)-F | 4.0% |
| 3-HB(F)CF2OB(F,F)-F | 4.0% |
| 4-HB(F)CF2OB(F,F)-F | 5.0% |

The properties of the above composition were as follows:

$T_{NI}$=71.5° C.
$T_C$<-20° C.
η=37.0 mpa·s
Δn=0.107
Vth=1.33 V
VHR=98.5%

EXAMPLE 10

There was prepared a liquid crystal composition comprising as a first component:

| | |
|---|---|
| 3-HHCF2OB(F,F)-OCF3 | 3.0% |
| 3-HHCF2OB(F,F)-CF3 | 3.0% |
| 3-HHCF2OB(F,F)-OCF2H | 3.0% |
| as a second component: | |
| 3-HHB(F,F)-F | 8.0% |
| 3-H2HB(F,F)-F | 8.0% |
| 4-H2HB(F,F)-F | 8.0% |
| 3-HBB(F,F)-F | 21.0% |
| 5-HBB(F,F)-F | 20.0% |
| 3-H2BB(F,F)-F | 10.0% |
| 5-HHBB(F,F)-F | 3.0% |
| 3-HH2BB(F,F)-F | 3.0% |
| and as another component: | |
| 5-HHEBB-F | 2.0% |
| 101-HBBH-4 | 4.0% |
| 101-HBBH-5 | 4.0% |

The properties of the above composition were as follows:

$T_{NI}$=100.0° C.
$T_C$<-20° C.
η=36.9 mpa·s
Δn=0.117
Vth=1.65 V
VHR=98.5%

As is seen from examples and comparative examples, the present invention provides a liquid crystal composition in particular which has a low threshold voltage and a wide range of nematic phase temperature (with high $T_{NI}$ point and low $T_C$), while satisfying various properties required for liquid crystal compositions for active matrix type liquid crystal display elements.

We claim:

1. A liquid crystal composition containing at least one of compounds represented by general formulas (1-1) and (1-2) as a first component, and at least one of compounds represented by general formulas (2-1) through (2-8) as a second component

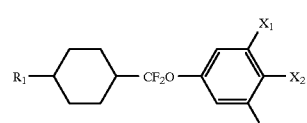
(1-1)

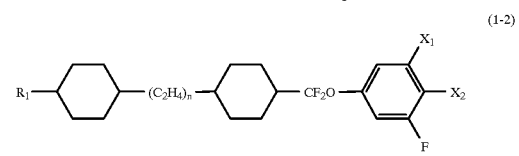
(1-2)

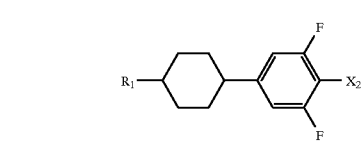
(2-1)

-continued

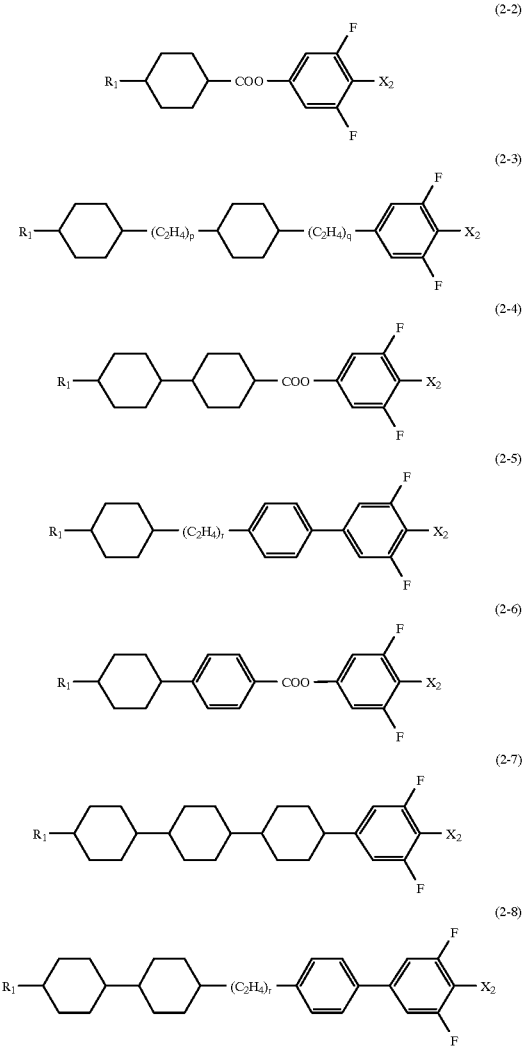

where each $R_1$ independently represents an alkyl group having 1 to 10 carbon atoms; each $X_1$ independently represents H or F; each $X_2$ independently represents F, $OCF_3$, $CF_3$, or $OCF_2H$; n represents 0 or 1; p and q independently represent 0 or 1; the sum of p and q is 1 or less; and each r independently represents 0 or 1.

2. A liquid crystal composition according to claim 1, wherein the total amount of compounds represented by general formulas (1-1) and (1-2) is 3 to 70 percent by weight relative to the total weight of the liquid crystal composition, and the total amount of compounds representedby general formulas (2-1) through (2-8) is 30 to 97 percent by weight relative to the total weight of the liquid crystal composition.

3. A liquid crystal composition according to claim 1 containing at least one of compounds represented by general formulas (1-1) and (1-2) in an amount of 3 to 70 percent by weight relative to the total weight of the liquid crystal composition as a first component, at least one of compounds represented by general formulas (2-1) through (2-8) in an amount of 27 to 94 percent by weight relative to the total weight of the liquid crystal composition as a second component, and at least one of compounds represented by general formulas (3-1) and (3-2) in an amount of 3 to 50 percent by weight relative to the total weight of the liquid crystal composition as a third component

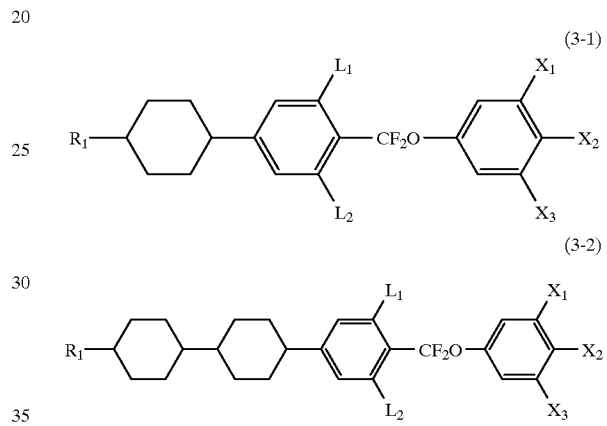

where each $R_1$ independently represents an alkyl group having 1 to 10 carbon atoms; $L_1$ and $L_2$ independently represent H or F; $X_1$ and $X_3$ independently represent H or F; and each $X_2$ independently represents F, $OCF_3$, $CF_3$, or $OCF_2H$.

4. A liquid crystal display element comprising composition according to claim 1.

5. A liquid crystal display element comprising a composition according to claim 2.

6. A liquid crystal display element comprising a composition according to claim 3.

* * * * *

UNITED STATES PATENT AND TRADEMARK OFFICE
CERTIFICATE OF CORRECTION

PATENT NO. : 5,961,881
DATED : October 5, 1999
INVENTOR(S) : Tugumiti Andou et al.

It is certified that error appears in the above-identified patent and that said Letters Patent is hereby corrected as shown below:

Column 8,
Line 65, delete the comma after "$R_1$".

Column 11,
Lines 45-51 Delete the entire formula and also delete the designation "(2-6-3)" after this formula.

Column 27,
Line 19, change "$R-(A_1)-Z_1-Z_n-(A_n)-X$" to -- $R-(A_1)-Z_1$ ------- $Z_n-(A_n)-X$ --.

Column 28,
Line 5, change "$R-(A_1)-Z_1-Z_n-(A_n)-X$" to -- $R-(A_1)-Z_1$ ------- $Z_n-(A_n)-X$ --.

Column 29,
Line 61, delete the comma after "$T_{NI}$".

Column 30,
Line 61, delete the comma after "$T_{NI}$".

Claim 2,
Line 1, change "Aliquid" to -- A liquid--.

Claim 4,
Line 1, after "comprising" insert -- a --.

Signed and Sealed this

Fourth Day of September, 2001

Attest:

NICHOLAS P. GODICI
Attesting Officer
Acting Director of the United States Patent and Trademark Office